United States Patent [19]

Cremins et al.

[11] Patent Number: 5,518,928
[45] Date of Patent: May 21, 1996

[54] LEUKOCYTE DIFFERENTIATION METHOD

[75] Inventors: John F. Cremins, Waterbury, Conn.; Joseph L. Orlik, Hopewell Junction, N.Y.

[73] Assignee: Bayer Corporation, Tarrytown, N.Y.

[21] Appl. No.: 934,517

[22] Filed: Jan. 28, 1987

Related U.S. Application Data

[63] Continuation of Ser. No. 638,179, Sep. 24, 1984, abandoned.

[51] Int. Cl.⁶ .................................................. G01N 31/00
[52] U.S. Cl. ................................ 436/40; 436/8; 436/11; 436/17; 436/18
[58] Field of Search ............................. 436/8–18, 519

[56] References Cited

U.S. PATENT DOCUMENTS 4,506,018  3/1985  North, Jr. .............................. 436/10
4,528,274  7/1985  Carter et al. ........................... 436/10
4,654,312  3/1987  Chang et al. .......................... 436/519
4,751,179  6/1988  Ledis et al. ............................ 436/10

*Primary Examiner*—James C. Housel
*Assistant Examiner*—Lien Tran
*Attorney, Agent, or Firm*—Andrew L. Klawitter

[57] ABSTRACT

A method is disclosed for differentiating white blood cells. The method uses at least one surfactant and at least one dilute acid which together selectively strip the cytoplasm from certain classes of white blood cells and not others. More particularly, the method causes lysis of lymphocytes, monocytes, eosinophils and neutrophils, but not basophils. Thus, basophils are differentiated from other PMN subclasses by their appearance as intact cells. The method totally avoids the need for dye preparation and the vagaries of staining techniques and can be used either manually or with instrumentation.

16 Claims, 12 Drawing Sheets

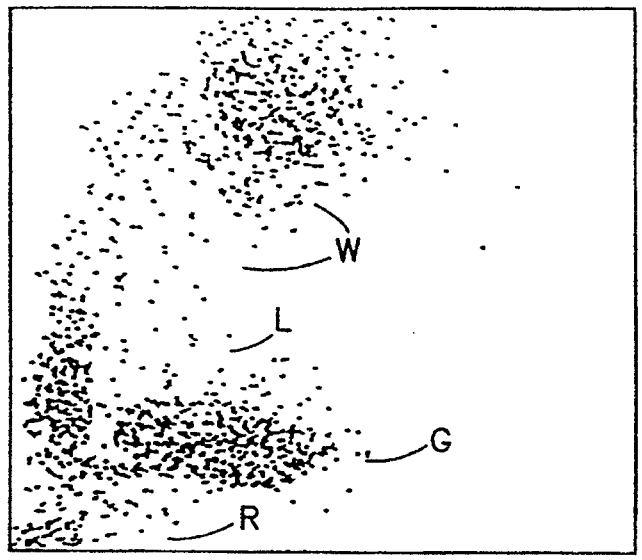
FIG. IC
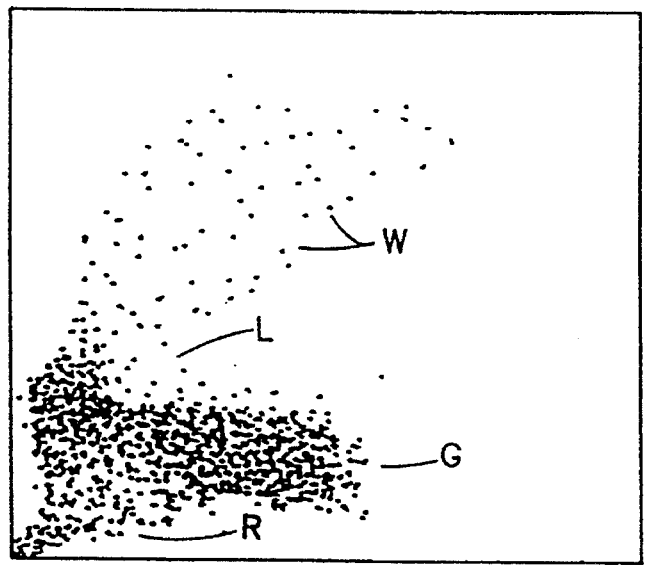
FIG. ID

H6000 BASOS

LEUKOCYTE DIFFERENTIATION METHOD

This application is a continuation of application Ser. No. 638179 filed Sep. 24, 1984 which is now abandoned.

BACKGROUND OF THE INVENTION

1. Field of the Invention

This invention relates to the field of hematology, particularly to differentiating subclasses of white blood cells.

2. Brief Description of the Prior Art

Human white blood cells are classified as lymphocytes, monocytes and polymorphonuclear cells (PMNs)o PMNs are sub-classified as neutrophils, eosinophils or basophils based on the staining characteristics of their cytoplasmic granules.

Differentiation of white blood cells has commonly been accomplished by various staining techniques. Several phthalocyanin compounds are known for use as such. The first of these to be discovered is called Alcian Blue. Alcian Blue has been used for the differential staining of basophils. The copper phthalocyanin cationic dyes are not sufficiently specific to achieve the selective staining of basophils when used alone because they also stain other cells which possess polynucleotides, e.g., DNA and RNA. In addition, basophils stain because of the unique presence in them of heparin, a sulfated polysaccharide. One way of establishing the desired selectivity is to combine it with lanthanum chloride which masks the polynucleotide phosphate groups and thereby prevents them from binding the phthalocyanin anion.

The use of Alcian Blue requires a closely controlled, highly acidic pH and it is heat labile. At alkaline pH and when exposed to heat, Alcian Blue forms particulates (insoluble dyes). This tendency to precipitate has been a longstanding problem in Alcian Blue-containing reagents. Automated analysis instruments contain components such as filters which collect these precipitates. This can interfere with the reliability of the determinations being made and even the operation of instruments on which this method is performed. It has nonetheless been considered the dye of choice because of its specificity and distinct color. For more background information on Alcian Blue, see Gilbert, et al, Basophil Counting With A New Staining Method Using Alcian Blue, Blood, 46:279–286 (1975).

Other phthalocyanin dyes have since been developed. For example, Bloom, et al, Histochemie, 2:48–57 (1960) shows the use of underivatized Astra Blue (free base) to stain biological tissues containing mucopolysaccharides, particularly mast cells. The Astra Blue free base is used in 0.5N HCl which gives it a positive charge. The low pH allows selectivity because of the inherent strength of sulfuric acid derivatives, e.g., heparin, which is ionized at pH 0.3, as compared to the weakness of phosphoric acid derivatives, e.g., DNA, which is not ionized at low pH.

Inagaki, Acta Hematologica Japonica, 32 (4):642–647 (1969), describes a method for staining basophil and mast cell granules using free base Astra Blue and a fixative solution of Acridine Orange in methanol containing 0.5M NaCl. Inagaki examined saturated cetyl pyridinium chloride in absolute methanol and saturated Acridine in absolute methanol for the fixation of peripheral blood and bone marrow smears. Cetyl pyridinium chloride securely preserved the basophil granules and the mast cell granules, but the Astra Blue staining tended to be prevented. Acridine could not preserve these cell granules sufficiently in the above described procedure.

In summary, Alcian Blue and Astra Blue free base and its quaternary derivatives have been the only compounds of this type which have been known to differentiate basophils from other white blood cells. The instability of Alcian Blue reagent has been a longstanding problem. Thus, workers in the field have continued to search for compounds which selectively stain basophils, in contrast to other white blood cells. Further, dye uptake is dependent on each individual user's staining technique.

Since cellular maturation is a continuous process, the successive stages involved are difficult to differentiate. However, separate stages can be recognized in whole blood smears stained with Wright's or Giemsa stains. This classification is based on the presence, nature and number of granules and the cytoplasmic and nuclear characteristics of each cell. These classifications of white blood cells and techniques for their differentiation are well known. See, for example, Ansley, et al, U.S. Pat. No. 3,741,875. However, classification of stained, intact cells based on cytoplasmic and nuclear information is very dependent upon subjective characterization by the user.

Kim, U.S. Pat. No. 4,099,917, has disclosed a method of preparing a blood sample for discrimination between classes of unstained white blood cells by their cell size and granularity characteristics. A blood sample is treated with a detergent which lyses red blood cells but does not lyse white cells, a fixative is added and the preparation is incubated. The cell suspension so obtained is said to allow differentiation of unstained, fixed, intact white cells by optical systems having low and high angle light scatter characteristics. This requires large complex instrumentation and, thus cannot be done by visual observation.

Ledis, et al, U.S. Pat. No. 4,286,963 discloses a composition comprised of (a) at least one long chain alkyl trimethyl quaternary ammonium salt, such as hexadecyl trimethyl ammonium bromide and (b) at least one additive selected from (i) a short chain alkanol substituted by phenyl or phenoxy, such as 2-phenoxyethanol and (ii) a polyhydroxy compound such as sorbitol for lysing red cells so that a differential determination of lymphoid and myeloid populations of white blood cells can be made.

Thus, most of the known techniques for this differentiation require the preparation and use of stains or provide for lysis only of red blood cells. Some require complex instrumentation. Otherwise, reported differentiation in whole cells, whether stained or unstained, is very much dependent upon subjective characterization. Nothing in the literature describes a reliable method for simultaneously determining an accurate basophil count and a lobularity index in the same sample of treated blood and in the absence of a stain.

Groner, et al, Blood Cells, 6:141–157 (1980) discusses differentiation of white blood cell subclasses using optical scatter, staining properties and other techniques. The concept of "left shift" is mentioned, referring to a trend in neutrophil populations toward more immature or less lobulated forms. A sharp change in index of refraction was created at the nuclear boundary by treating a whole blood sample with a strong cationic detergent and maleic acid. As a result, the red blood cells were lysed, most of the cytoplasm of the leukocytes was leached, and the nucleus shrank slightly. From the discussion in this reference, it appears that the leukocyte membranes were not ruptured or lysed (as mentioned with reference to red blood cells), leukocyte cytoplasm was not completely (only mostly) stripped leaving artifacts which distort the apparent shape of the nucleus and, finally, there is no mention of differentiation of the effect of this treatment between one leukocyte subclass and any other.

SUMMARY OF THE INVENTION

In contrast to the techniques offered by the prior art and in accordance with the present invention, it is now possible to provide a precise characterization of nuclear morphology (lobularity) and to differentiate among sub-classes of PMNs based on the cytoplasmic stripping of certain sub-classes and not others. The composition selectively removes cytoplasm from certain classes of white blood cells and not others. More particularly, the composition causes cytoplasmic removal from lymphocytes, monocytes, eosinophils and neutrophils, but not basophils. Thus, basophils are differentiated from other PMN sub-classes by their retention of granules and cytoplasmic membrane. In addition, since nucleated red blood cells are detected, the invention allows for their quantitation as well.

The potential error arising from cytoplasmic artifacts adhering to the nuclei of all blood cells other than basophils, thus altering the apparent shape of the nuclei, is avoided by complete stripping of cytoplasmic material from their nuclei by the composition of the invention. As such, differentiation of blast cell, nucleated red cells and of the various maturation stages of neutrophils, based on their nuclear morphology, can be made with certainty. An important advantage is that the composition and method totally avoid the need for dye preparation and the resulting vagaries of staining techniques. The composition described can be used manually or with instrumentation.

The composition of the invention for differentiation of white blood cells in a sample comprises at least one water-soluble surfactant and at least one dilute acid effective to strip cell membranes and cytoplasm from selected sub-classes of white blood cells and not others, and has a pH of from about 1.8 to about 2.3. The surfactant can, for example, be a $C_6$–$C_{16}$ aliphatic alcohol ether of a poly alkylene glycol. The acid is preferably a sulfonic or carboxylic acid or hydrochloric acid.

The invention further provides a method for differentiating subclasses of white blood cells. A blood sample is treated to strip the cell membranes and cytoplasm from selected subclasses of white blood cells and the subclasses are then differentiated based on their nuclear morphology. More particularly, the membrane and cytoplasm are completely stripped from all subclasses of leukocytes other than basophils.

BRIEF DESCRIPTION OF THE DRAWINGS

FIGS. 1A–1E are two-dimensional distribution plots of the scattering patterns of individual white blood cells in cell suspensions analyzed, using a composition of the invention, in a flow cytometer. Each white blood cell is represented by a black dot and each plot shows the observed patterns at a successive stage of the reactions carried out in the experiments described in Example II.

DESCRIPTION OF THE PREFERRED EMBODIMENTS

Figure 1A:
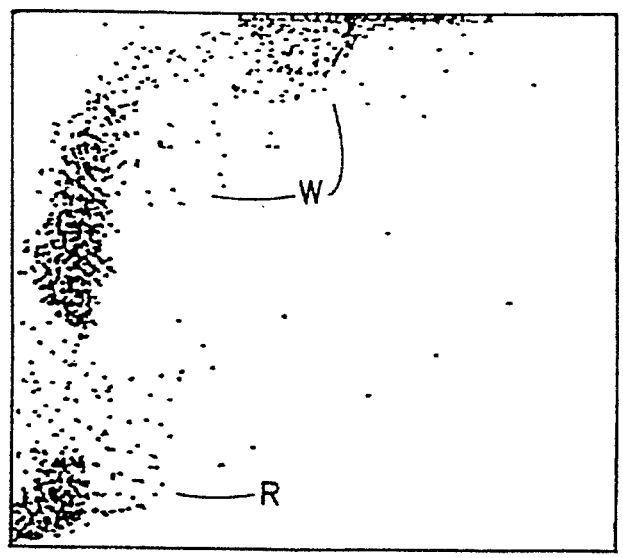

Specific terms in the following description, which refer to only a particular embodiment, are exemplary of all of the embodiments unless otherwise indicated.

As previously indicated, the composition of the invention selectively strips the cytoplasm of certain classes of white blood cells and not others. Lymphocytes, monocytes, eosinophils and neutrophils are cytoplasmically stripped. That is, their membrane and cytoplasmic material are stripped from their nuclei which are left unaffected and free of associated cytoplasmic material. Thus, the morphology of their nuclei is sharply defined. In contrast to the cytoplasmic removal so affected, basophils retain their granules and cytoplasmic membrane.

The novel composition of this invention finds application in manual or flow cytometric detection of various blood cell types. The composition disclosed herein is comprised of a water-soluble surfactant and a dilute acid and has a pH range of from about 1.8 to about 2.3. It can also, optionally, include an antioxidant. For performance-of the assay, the surfactant and dilute acid component(s) must be present. Omission of either component yields a non-functional composition. The chain terminating antioxidant prevents autoxidative degradation of the surfactant which leads to deterioration of the cytoplasmic stripping function. In the absence of the antioxidant, the composition shelf-life is two months when stored at 25° C. However, when the antioxidant is present, the shelf-life is at least one year at 25° C. The antioxidant does not interfere with proper functioning of the composition.

The water soluble surfactant can be any surfactant which provides the required action on blood cells: complete lysis of red cells and platelets, loss of cytoplasm and cell cytoplasmic membrane of neutrophils, eosinophils, lymphocytes and monocytes and retention of granules and cell membrane for basophils. Examples include: (i) $C_6$–$C_{16}$ aliphatic alcohol ethers of a polyalkylene.

The invention also requires the presence of at least one dilute acid. Examples include: (i) organic sulfonic acids, such as methane sulfonic acid or ethane sulfonic acid; (ii)

carboxylic acids, such as maleic, phthalic, oxalic, malonic, glycine, dichloroacetic and lactic acids; and (iii) mixtures thereof. It can also be advantageous to use at least one dilute inorganic acid. Examples include hydrochloric, hydrobromic, sulfuric and phosphoric acid. For present purposes, "dilute" refers to concentrations of about 30 mM or less. Particularly useful are combinations of mineral acids and carboxylic acids, such as phthalic acid-HCl.

The reagent composition, as used in analyzing samples with which it is contacted, must have a pH range of from about 1.8 to about 2.3. Although this is a narrow pH range, it is an important aspect of the invention. This pH can be established by the presence of the dilute, acid, alone, or can be effected by including additional acids.

The composition can also, optionally, include a chain-terminating antioxidant which will retard the degradation of the surfactant as a result of autoxidation, thus enhancing shelf life. The antioxidant destroys peroxy radicals which, if not inhibited, would participate in chain reactions. Examples include di-tert-butyl-4-methylphenol (BHT), p-methoxy phenol (MEHQ) or di-tert-butyl-4-methoxyphenol (BHA).

The composition can also, optionally, include an antimicrobial preservative which will retard or prevent the growth of contaminating organisms such as mold.

In the preferred embodiments of this invention, the ingredients are used in the proportionate ranges:

a) surfactant 10–20 g/l b) dilute acid 0.020–0.024 M/l c) chain terminating antioxidant 0.1–0.2 g/l d) antimicrobial preservative 0.2–0.6 g/l It is desirable to be able to control the reaction rate so that the method can be optimized for either manual or automated modes. In this regard, compositions comprised of Brij-35, maleic acid and BHT are of particular interest. Maleic acid may be utilized over a concentration range of 0.025%–1% (0.0022–0.086M). The effect of variation of the maleic acid concentration leads to a net increase in the rate of about tenfold.

The lower range of concentration of maleic acid is particularly useful for manual microscopic work. The reaction rate is slow enough such that the procedure can be accomplished within two minutes. In contrast, at the higher end of the range, the reaction is essentially instantaneous and is appropriate for automated instrumental techniques.

In practicing the method of the invention, it has been observed that when whole blood is mixed with a solution of surfactant and dilute acids, there is a sequence of membrane and cytoplasmic destruction which begins with red blood cell lysis leaving no structure of the red blood cell behind, platelet lysis which also leaves no structure behind, and white blood cells cytoplasmic stripping leaving bare nuclei of all white blood cells but for basophils which remain substantially intact as the only whole cells observable in the treated blood sample. The white blood cell nuclei and the basophils which retain their cytoplasmic membrane and granularity can be differentiated by visual observation or through an instrumental detection system.

It is preferred to introduce the cell sample into a fluid stream flowing in a conduit or analysis channel in a flow cytometer. This preferably comprises establishing a flowing stream of a sheath fluid in the conduit or analysis channel and thereafter introducing the sample into the flowing sheath stream. Such sheath streams are usually of fluids having a refractive index substantially identical to that of the cell sample suspending medium. One such flow cytometer which uses a sheath stream carrier fluid is used in the Technicon Hemalog D and H-6000 systems, which handle all routine hematology tests. Detailed information on the Hemalog D and H-6000 systems is available from Technicon Instruments Corporation, Tarrytown, N.Y.

The following working examples describe experiments which were performed in developing the present invention. In summary, the results in these examples demonstrate that the composition and method of the invention make it possible to (a) obtain accurate basophil counts; (b) provide an indication of the mean lobe count or amount and severity of left shift present in any given sample; (c) obtain accurate differentiation of blast cells from other mononuclear cells; (d) quantitate and identify nucleated red blood cells; and (e) obtain a total white blood cell count. Standard commercially available reagent grade chemicals were used whenever possible.

EXAMPLE I

MANUAL DIFFERENTIAL WHITE BLOOD CELL COUNT

A differential white blood cell (WBC) count is one of the most important distinguishing parameters in the differential diagnosis of various disease states, particularly relating to infectious and immunological disorders. In the experiment reported by this example the composition of the invention was prepared and used in differentiating basophils from all other blood cells and mononuclear from polymorphonuclear white blood cells.

The composition of the invention was prepared in 97 milliliters (ml) of distilled water by adding 0.20 grams (g) of maleic acid and 3 ml Brij-35 (made to 30% weight/volume (w/v) in distilled water).

An 8.0 microliter (ul) sample of fresh whole human blood was mixed with 500 ul of the composition prepared as described above. After one minute an aliquot of the reacted whole blood sample was pipetted onto a clean microscope slide for observation under 40× power through a Nikon microscope.

Upon microscopic examination of this aliquot it was observed that the red blood cells and platelets were destroyed and white blood cells, other than basophils, of the sample had been completely cytoplasmically stripped. The cytoplasmic membrane and granules of basophilic PMNs had been unaffected and remained intact.

Compositions were also prepared which were like those described above but for the absence of maleic acid. This composition was used for testing blood samples as described above and no lysis of blood components was observed. Also, compositions were prepared in which maleic acid was present, but the surfactant, Brij 35, was omitted. Cellular clumping was observed to occur which obscured recognition of basophils and of white blood cell lobularity. As such, neither of these compositions was effective to provide the differentiation made possible by the composition of the invention.

EXAMPLE II

AUTOMATED DIFFERENTIAL WHITE BLOOD CELL COUNT

The experiments reported in this example show the use of the composition of the invention in making an accurate basophil count. Basophils, mononuclear cells (immature granulocytes, lymphocytes and monocytes) and PMNs (neutrophils and eosinophils) were determined. They were compared (correlated) with the same determinations made by existing techniques as used on the H-6000 instrument system (Technicon, supra). A determination of the presence of immature granulocytres is illustrated. Also, the composition of the invention was used to determine left shift, e.g., decrease in mean neutrophil lobe count.

A reagent composition was prepared, in accordance with the invention, to contain 3.6 g pthalic acid, 10 g Brij-35; 0.1 g BHT; 1.0 ml of 1N HCL; and was made up to 1 liter with distilled $H_2O$ (pH 2.0).

Blood samples from each of a large panel of patients were examined using the same test procedure for each. An 8 ul volume of each blood sample was placed in a separate test tube along with 500 ul of the above reagent composition. After 50 seconds of mixing, the reaction mixture was peristaltically pumped through a sheath stream flow cell at a flow rate of 0.1 ml/min.

The optical system used to obtain two-dimensional distributions of cell-by-cell light scattering signatures was that of a modified RBC/PLT channel of a Technicon H-6000 flow cytometry system (Technicon, supra). High angle scatter was measured along the abscissa and low angle scatter was measured along the ordinate in the output provided by the system. Threshold lines of demarcation were set by computer using cluster analysis to distinguish between various cell types and the system was programmed to ignore all the signals due to cellular debris and the like. A complete description of the optics system used is available from Technicon, supra. The output signals from this optics system were amplified and converted into a two-dimensional distribution plot. Each dot represented the measured coordinates of a single cell.

Figure 1B:
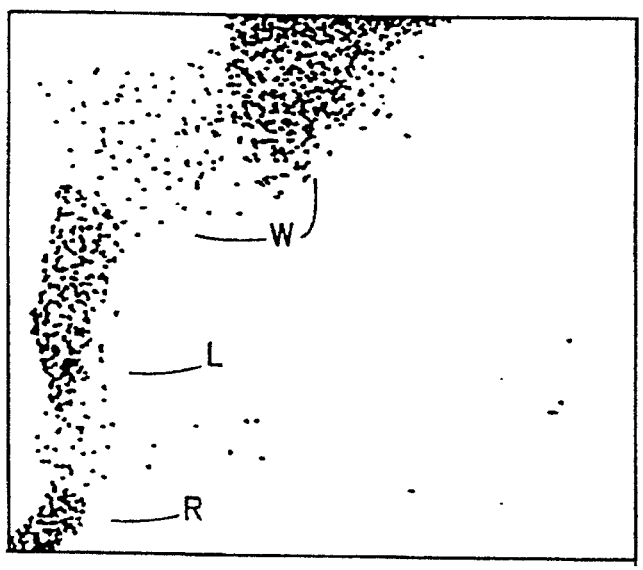
Figure 1E:
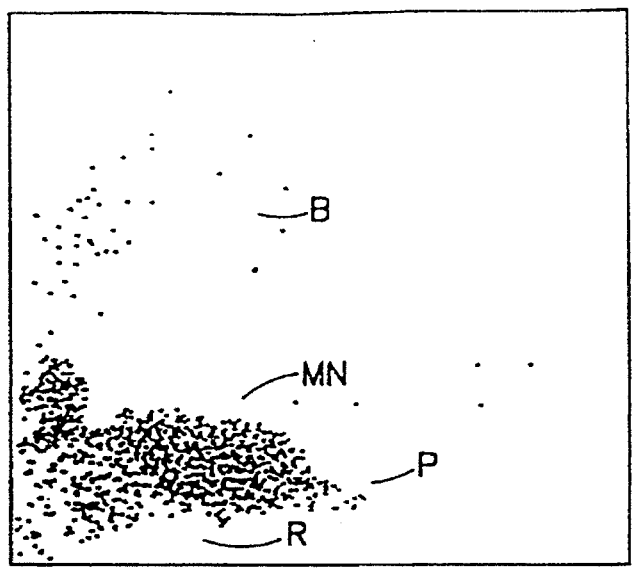

Each of the samples taken from the panel of patients was analyzed using the above composition and procedure in accordance with the invention. FIGS. 1A–1E represent the stages of the reaction from the above analysis procedure on one of such samples, from a normal donor, at different time intervals from initiation of the reaction. FIG. 1A (15 seconds) shows RBCs and PLTs which have been destroyed (R) and swollen WBCs (W). FIG. 1B (20–25 seconds) shows lymphocytes (L) which have started to lose their cytoplasm and move along the Y-axis toward the origin. In FIG. 1C (30–35 seconds) some granulocytes (G) have begun to lose their cytoplasm and all lymphocytes (L) have undergone complete cytoplasmic stripping. In FIG. 1D (40–45 seconds) most granulocytes (G) and all lymphocytes (n) have been completely cytoplasmically stripped and, thus, have moved to their final X-Y positions. A few WBCs (W), mostly monocytes, remain intact. FIG. 1E (80 seconds) shows that all white blood cells, except for basophils (B), have been stripped of their cytoplasm, leaving only bare nuclei, and are in their final X-Y positions. Distinct clusters of PMNs (P), mononuclear cells (MN), basophils (B), and cellular debris (R) are shown.

The samples taken from the panel of patients were also tested on a conventional, commercially available Technicon H-6000 system in accordance with the manufacturer's directions. The correlation of the results for each of the basophil, mononuclear cell (MN) and PMN clusters is represented by FIGS. 2–4, respectively.

Figure 2:
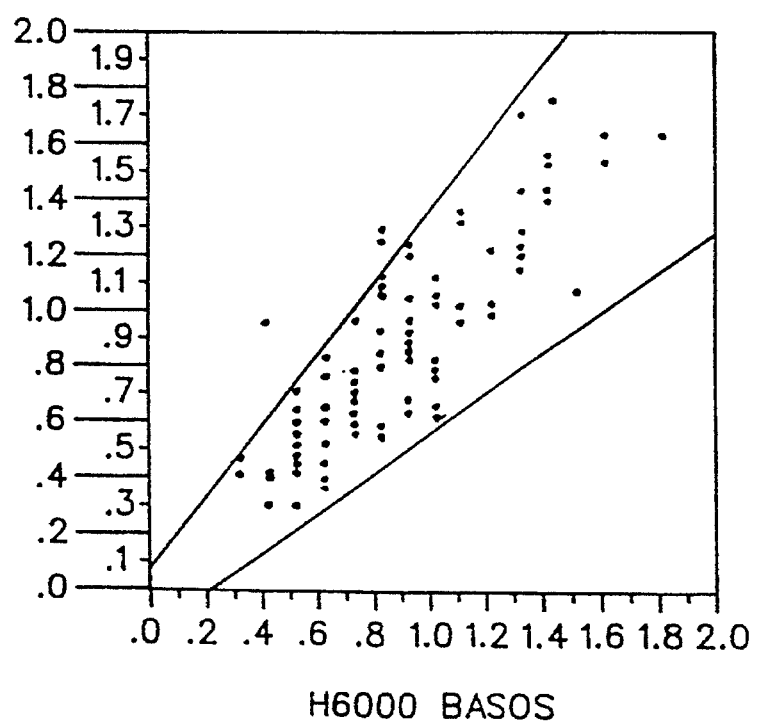
FIG. 2 is a two-dimensional distribution plot showing the distribution of basophil counts (not individual cells) in samples tested as described in Example II.

FIG. 2 shows a Rumpke Oval placed on the data from 98 samples, normal and abnormal, comparing the method of the invention against the Technicon H-6000 basophil chemistry for percent basophils. This Figure shows excellent agreement along with the fact that more than 95% of the points fall within the oval. A correlation coefficient of 0.81 was observed.

Figure 3:
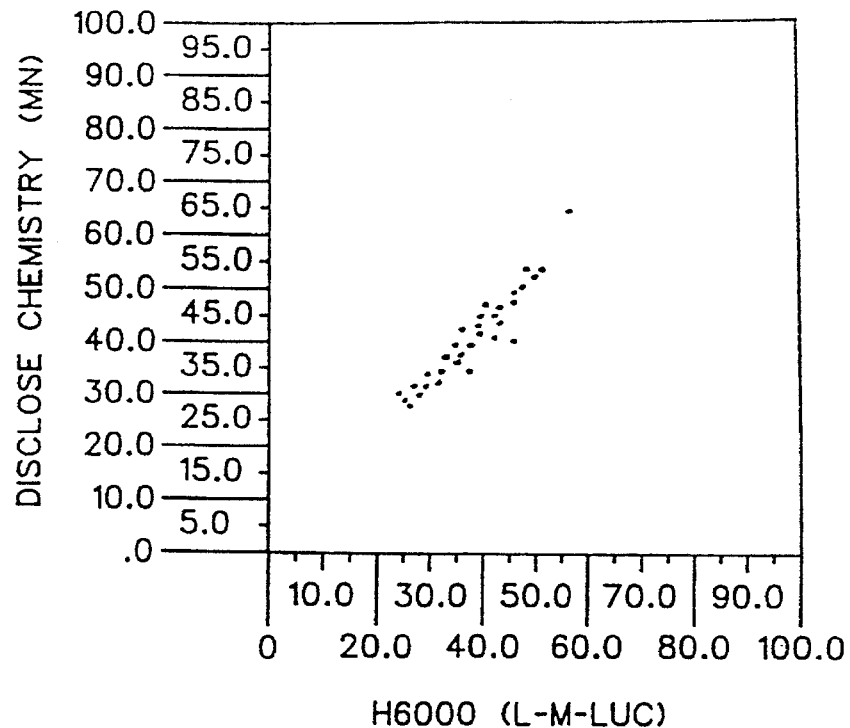
FIG. 3 is a two-dimensional distribution plot showing the distribution of mononuclear cell counts (not individual cells) in samples tested as described in Example II.

FIG. 3 shows excellent accuracy and correlation for mononuclear cells (MN) using the disclosed chemistry and mononuclear cells, including lymphocytes (L), monocytes (M) and large unstained cells (LUC), using the Technicon H-6000 peroxidase chemistry. The number of samples was reduced to eliminate abnormal (leukemic) samples to indicate how well the method of invention agrees on normal samples. A correlation coefficient of 0.96 was observed.

Figure 4:
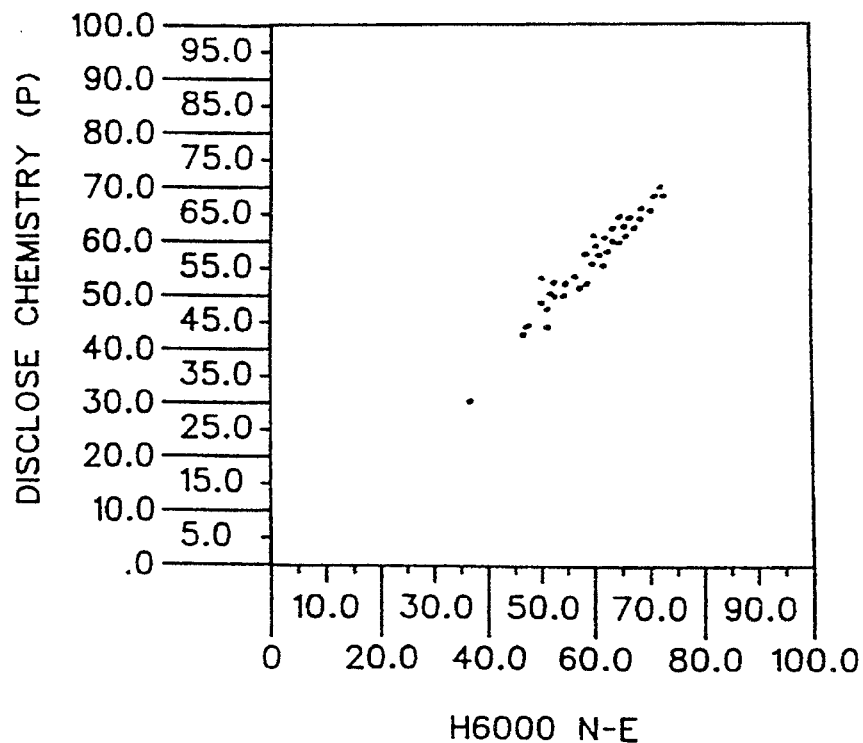
FIG. 4 is a two-dimensional distribution plot showing the distribution of polymorphonuclear cell counts (not individual cells) in samples tested as described in Example II.

FIG. 4 shows the excellent accuracy and correlation for PMNs on the same samples reported, using the disclosed chemistry (P) and the H-6000 system, which reports PMNs as neutrophils (N) and eosinophils (E). A correlation coefficient of 0.97 was observed.

Figure 5A:
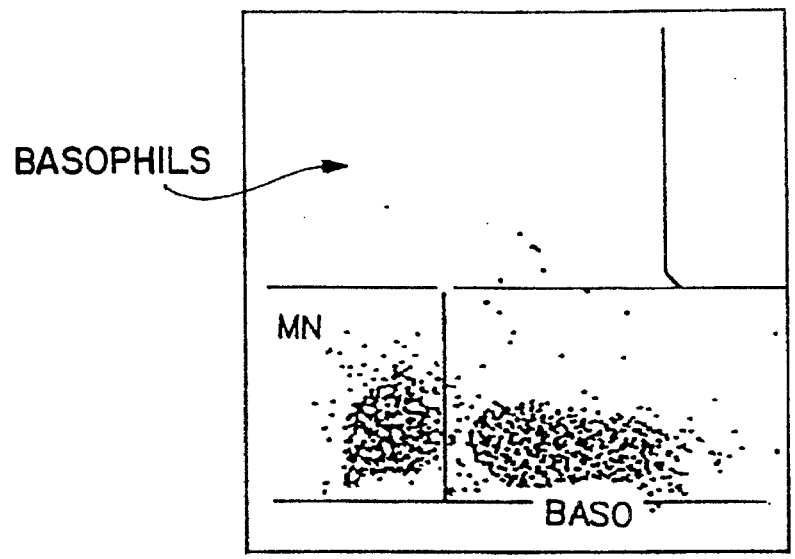
FIGS. 5A–5B are two-dimensional distribution plots of an abnormal whole blood sample known to contain immature granulocytes which were obtained using the composition of the invention and a conventional methodology, respectively.
Figure 5B:
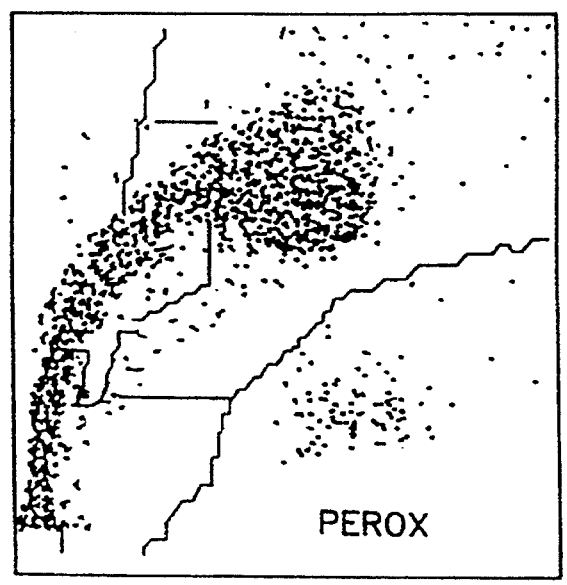

FIGS. 5A and 5B are two-dimensional distribution plots of an abnormal sample known to contain immature granulocytes using the disclosed chemistry and the conventional H-6000 system peroxidase chemistry, respectively. A more densely populated cluster of mononuclear cells is observed in FIG. 5A, than would be expected from the peroxidase-chemistry lymphocytes, monocytes plus large unstained cells. The percentage of cell types reported using each of the above methods, and as observed manually, is set forth in Table I.

TABLE I

|  | Mononuclear | PMN | Immature G |
|---|---|---|---|
| Discl. Chem. | 39.6% | 57.9% | NA |
| H-6000 | 31.6% | 67.7% | NA |
| Manual | 33.5% | 59.0% | 7.5% |

The substantial difference in the number of mononuclear cells observed between the disclosed method and H-6000 method corresponds with the number of immature granulocytes observed by the manual method. Therefore, samples containing significant numbers of immature granulocytes can be distinguished from normal samples.

Figure 6A:
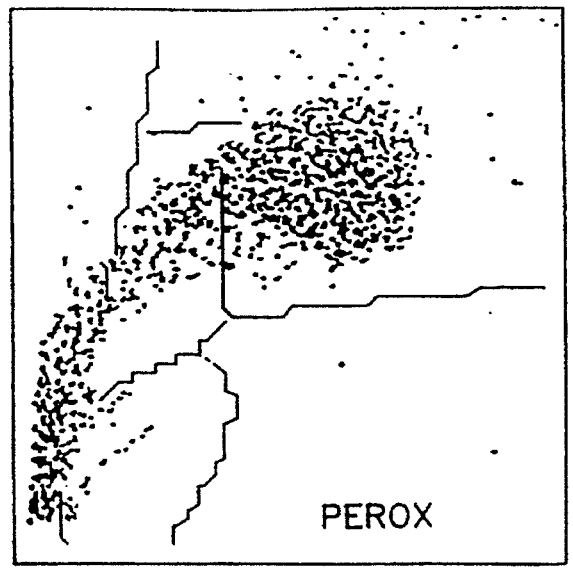
FIGS. 6A–6F are two-dimensional distribution plots illustrating the ability of the disclosed chemistry to indicate left shift as compared to a conventional methodology.
Figure 6B:
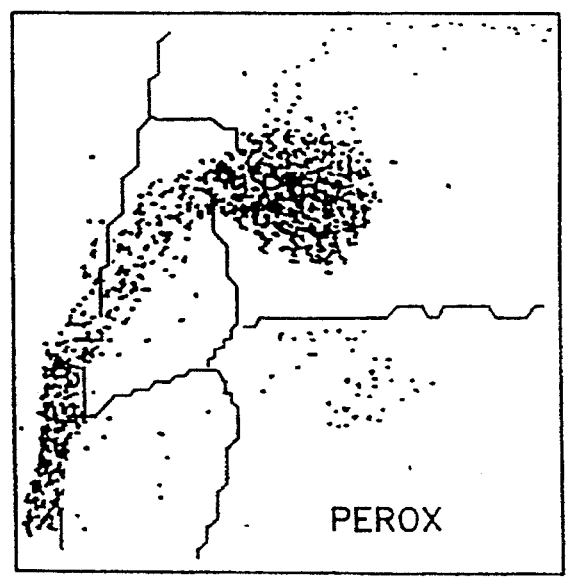
Figure 6C:
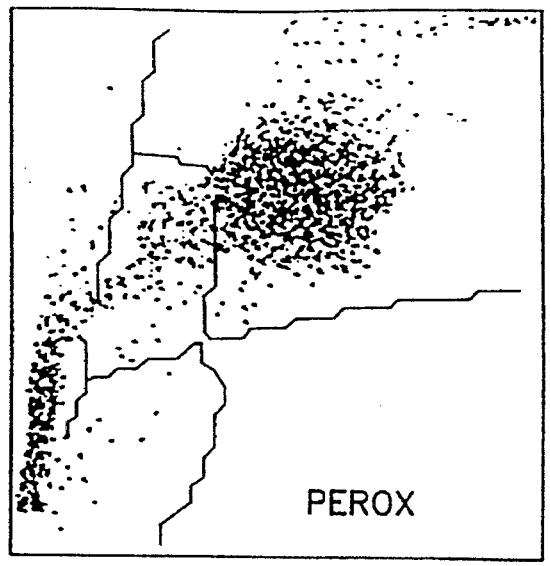
Figure 6D:
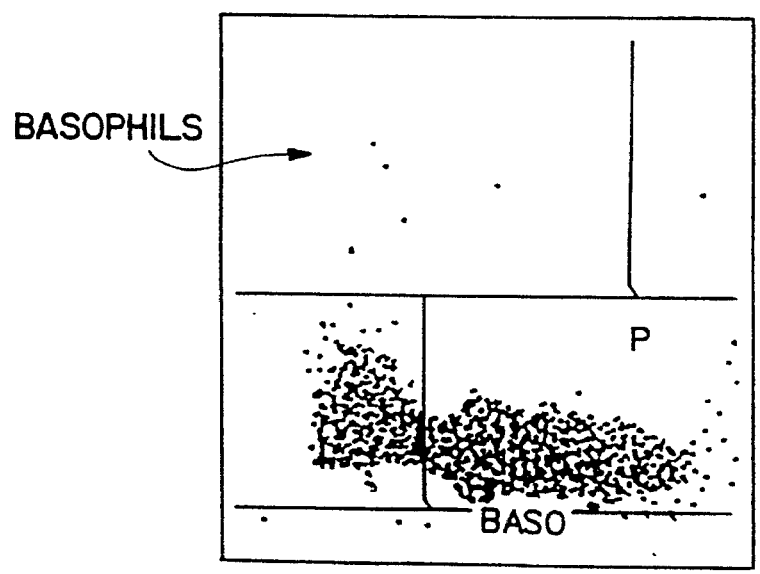
Figure 6E:
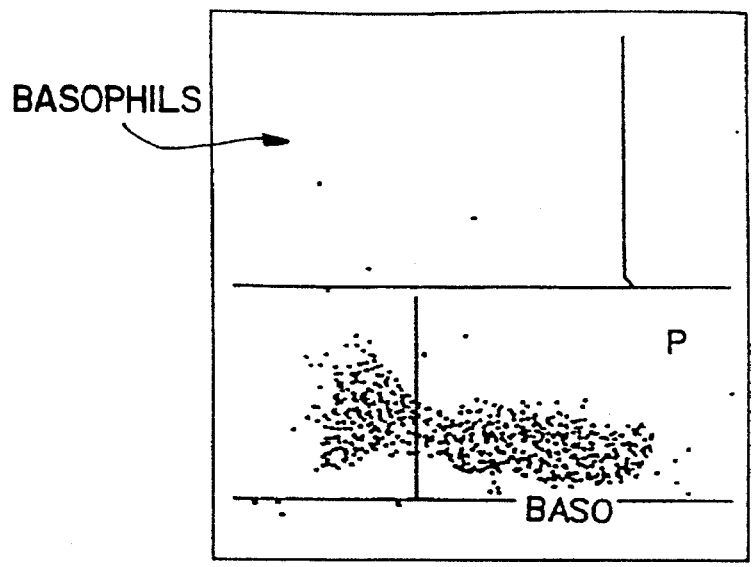
Figure 6F:
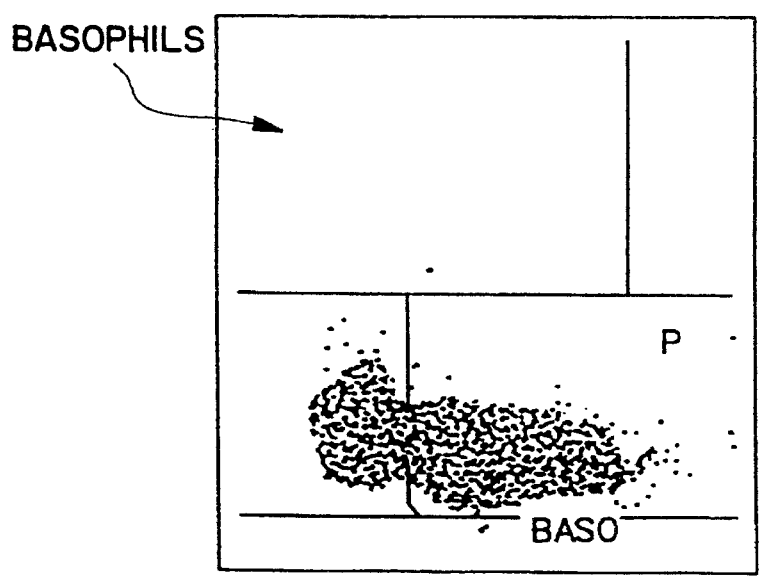

Another benefit of the disclosed chemistry, because of the preservation of only the nuclei of the neutrophil, is its ability to indicate the presence of a left shift (i.e., a decrease in the mean neutrophil nuclear lobe count caused by the presence of a greater number of band cells). This is demonstrated by the fact that as the mean lobe count decreases, the mode of the PMN cluster (P) decreases. FIGS. 6A–6C show the H-6000 method for three samples with increasing band counts and decreasing mean lobe counts. It can be seen that these three samples have no distinguishing characteristics to suggest which sample has the left shift. FIGS. 6D–6F show the same samples using the disclosed chemistry. It can be seen that as the mean lobe count decreases, there is a corresponding decrease in the mode of the PMN cluster (P). This movement to the left of the PMN cluster mode allows the disclosed chemistry to predict the presence of a left shift. Table II shows the manual band count and manual mean neutrophil lobe count versus the mode of the PMN cluster (P) for these samples, ranging from 0–20 band cells and mean lobe counts from 3.38 down to 2.31.

TABLE II

| Manual Band Count | Manual Mean Lobe Count | PMN Mode |
|---|---|---|
| 0% (FIG. 6D) | 3.38 | 30.5 |
| 5% (FIG. 6E) | 3.06 | 27.0 |

TABLE II-continued

| Manual Band Count | Manual Mean Lobe Count | PMN Mode |
|---|---|---|
| 20% (FIG. 6F) | 2.31 | 24.5 |

EXAMPLE III

The experiments reported in this example show the use of the same composition and method of analysis of the invention as described in Example II for differentiating blast cells from other mononuclear cells. Significant percentages of large unstained cells observed using the H-6000 system peroxidase chemistry have been attributed to the presence of abnormal mononuclear cells. Such methods have not been able to identify these as either blast cells or atypical lymphocytes.

Whole blood samples were obtained from a donor with acute myeloblastic leukemia (sample A), a normal donor (sample B) and a donor with chronic lymphocytic leukemia (sample C). The pattern of cell clusters for each when analyzed using the composition of the invention is illustrated by FIGS. 7D–7F, respectively.

Another aliquot of each of these same three samples was stained for peroxidase activity and analyzed using the conventional peroxidase reagents and channel on an H-6000 system. The results reported are illustrated in FIGS. 7A–7C, respectively.

Figure 7A:
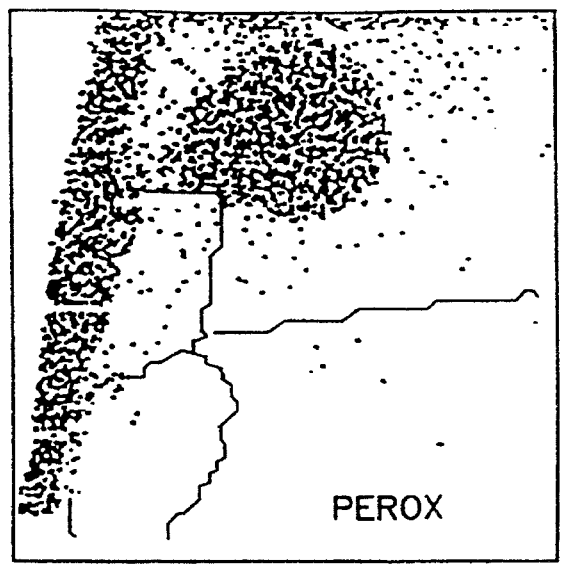
FIGS. 7A–7C are two-dimensional distribution plots of the experiments performed in Example III using a conventional methodology.
Figure 7B:
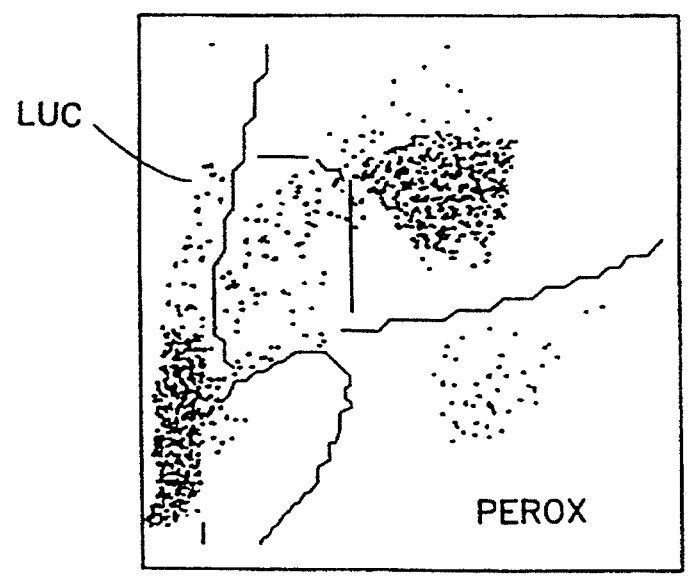
Figure 7C:
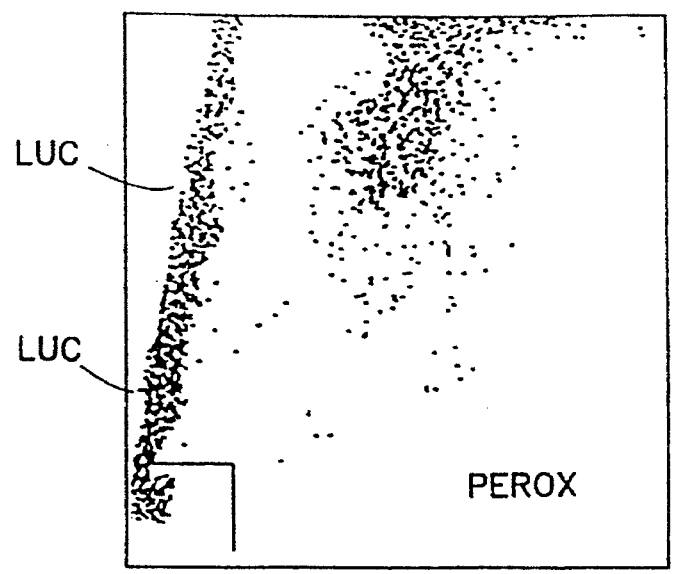

FIGS. 7A and 7C both show a substantial population of large unstained cells (LUCs). As such, they are indicative of the presence of abnormal mononuclear cells and can be differentiated from FIG. 7B, representing the normal population distribution. However, FIGS. 7A and 7C appear substantially identical to one another, thus providing no way to determine whether these increased LUC populations are due to an increase in blast cells, indicative of acute myeloblastic leukemia, or atypical lymphocytes, indicative of chronic lymphocytic leukemia.

Figure 7D:
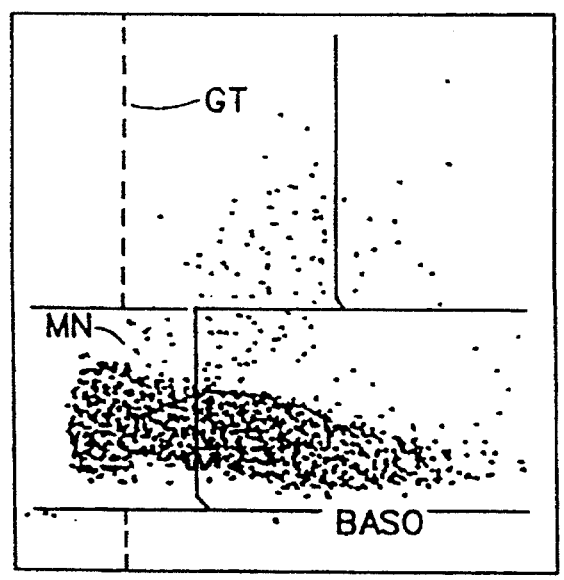
FIGS. 7D–7F are two-dimensional distribution plots of individual blood samples analyzed, using a composition of the invention, in a flow cytometer. They illustrate the results obtained in the experiments of Example III on samples from a donor with acute myeloblastic leukemia, a normal donor and a donor with chronic lymphocytic leukemia, respectively.
Figure 7E:
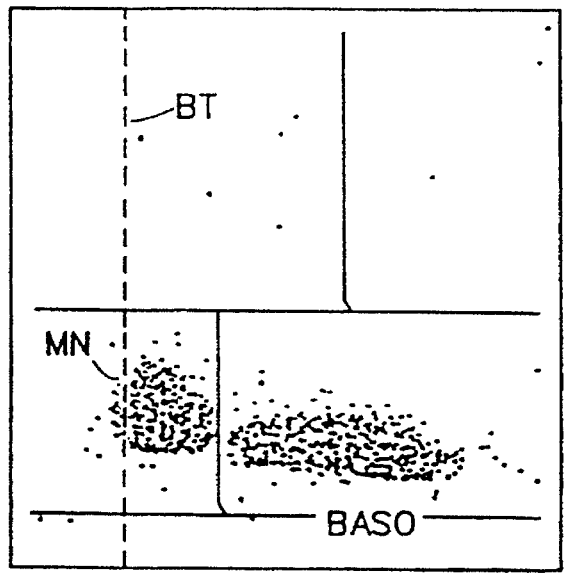
Figure 7F:
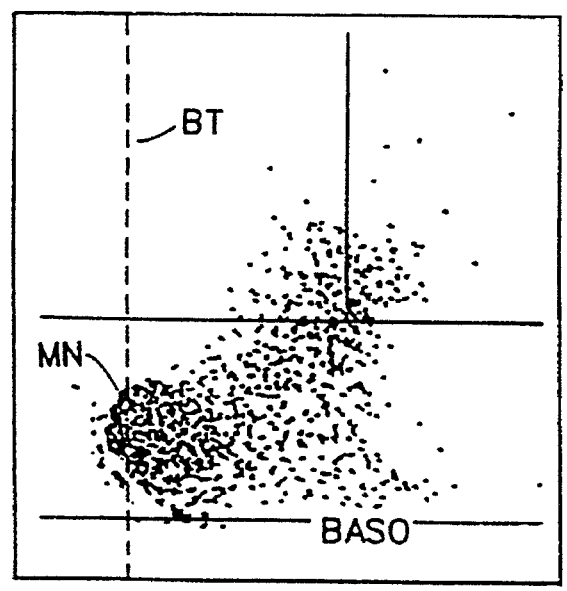

FIGS. 7D and 7F show a significant difference in the position of the mononuclear (MN) clusters as they appeared along the X axis. The MN cluster in FIG. 7D, having moved to the left, toward the origin, contains the blast cells. In contrast, the MN cluster in FIG. 7F remained in the same position as that of the MN cluster in FIG. 7E, which is that of the normal donor. By placing a fixed, vertical blast threshold (BT) one can obtain an accurate last percent.

The percentages of blast cells observed, using a manual method and the disclosed chemistry, and the percentage of large unstained cells using the H-6000 chemistry are Shown in Table III.

TABLE III

| % Blasts | | % LUCs |
|---|---|---|
| Manual | Disclosed | H-6000 |
| 22.0% | 23.18% (FIG. 7D) | 31.4% (FIG. 7A) |
| 0% | 0.64% (FIG. 7E) | 2.3% (FIG. 7B) |
| 0% | 0.17% (FIG. 7F) | 41.2% (FIG. 7C) |

Thus, it has been demonstrated that, using the composition of the invention, it is now possible to distinguish between blast cells and atypical lymphocytes. This provides a mode of differentiating between significantly different classes of leukemias.

EXAMPLE IV

The experiment reported in this example used the same composition and method of analysis as described in Example II. For quantitatively determining nucleated red blood cells (NRBC) the presence of immature, nucleated red blood cells in circulating blood is a significant abnormal finding which, until now, could not be instrumentally determined.

Figure 8A:
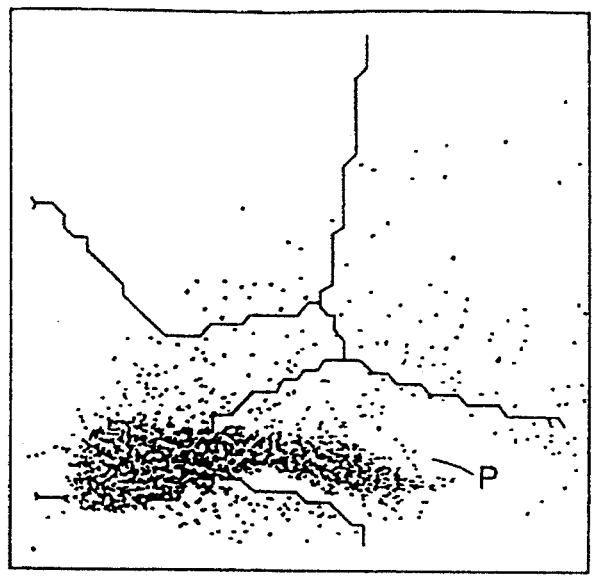
FIGS. 8A–8B are two-dimensional distribution plots of the scattering patterns of individual white blood cells in cell suspensions passed through a flow cytometer using a composition in accordance with the invention and a conventional peroxidase reagent, respectively, as described in Example IV.
Figure 8B:
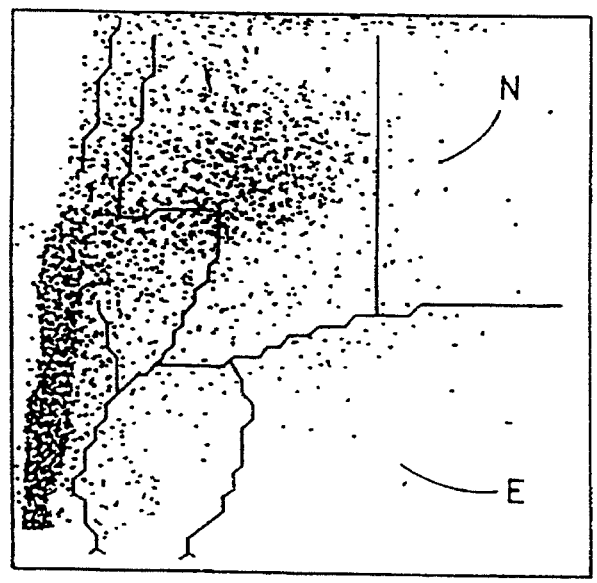

A sample of whole blood containing nucleated red blood cells was mixed with the composition of the invention and analyzed. The results are shown in FIG. 8A. A dense cluster of cells appears in the PMN region (P). Another aliquot of the same sample was stained for peroxidase activity and analyzed using the conventional peroxidase reagents and channel on an H-6000 system. The results obtained were as shown in FIG. 8B. Only scattered cells appeared in the region where neutrophils (N) and eosinophils (E) usually appear.

Thus, the conventional peroxidase methodology detects almost no PMNs, while the method of the invention detects a significant PMN population which proved to be the nucleated red cells, as confirmed by visual examination. This proved to be the difference in the absolute cells per lambda between the PMN cound using the conventional H-6000 system methodology and the PMN count using the method of the invention.

What is claimed is:

1. A method of identification of subclasses of leukocytes comprising:

a) providing an aliquot of a whole blood sample;

b) reacting the erythrocytes and the neutrophils, eosinophils, lymphocytes, monocytes and basophils in said aliquot with a reagent which comprises the mixture of an aqueous solution of:

i) at least one water-soluble non-cationic surfactant; and ii) at least one acid to render the reagent acidic;

to thereby lyse the erythrocytes and strip the cytoplasm and cell cytoplasmic membrane from the nuclei of said neutrophils, eosinophils, lymphocytes and monocytes, and retain the granules and cell cytoplasmic membranes of said basophils as intact cells;

c) thereafter exposing said aliquot reagent mixture of step b) to an area of focused optical illumination;

d) observing the optical characteristics of said nuclei and cells; and e) differentiating said nuclei and cells of subclasses of leukocytes at least in part on the basis of their observed optical characteristics.

2. The method of claim 1 wherein said non-cationic surfactant is a $C_6$–$C_{16}$ aliphatic alcohol ether of a polyoxyethylene glycol.

3. The method of claim 1 wherein said at least one acid maintains the pH of said reagent at from about 1.8 to about 2.3.

4. The method of claim 1 wherein said at least one acid is a mineral acid.

5. The method of claim 1 wherein the at least one acid includes a carboxylic acid selected from the group consisting of maleic, phthalic, oxalic, malonic, dichloroacetic and lactic acid and glycine.

6. The method of claim 1 wherein said reagent further comprises a chain-terminating antioxidant.

7. The method of claim 1 wherein said reagent further comprises an anti-microbial preservative.

8. A flow cytometry method for identifying and enumerating subclasses of white blood cells in a heterogeneous whole blood cell suspension based upon measurement of the scattering properties of the nuclei of the mononuclear and polymorphonuclear cells and the intact basophils of interest, which method comprises:

a) providing an aliquot of a whole blood sample;

b) reacting the erythrocytes and the neutrophils, eosinophils, lymphocytes, monocytes and basophils in said aliquot with a reagent which comprises the mixture of an aqueous solution of:
   i) at least one water-soluble non-cationic surfactant; and
   ii) at least one acid to render the reagent acidic;
   to thereby lyse the erythrocytes and strip the cytoplasm and cell cytoplasmic membrane from the nuclei of said neutrophils, eosinophils, lymphocytes and monocytes, and retain the granules and cell cytoplasmic membranes of said basophils as intact cells;

c) thereafter passing said aliquot reagent mixture of step b) substantially a particle at a time through an area of focused optical illumination and detecting the light scattered by each nucleus or cell; and d) differentiating said nuclei and cells of subclasses of leukocytes at least in part on the basis of said scattered light.

9. The method of claim 8 wherein said non-cationic surfactant is a $C_6$–$C_{16}$ aliphatic alcohol ether of a polyoxyethylene glycol.

10. The method of claim 8 wherein said at least one acid maintains the pH of said reagent at from about 1.8 to about 2.3.

11. The method of claim 8 wherein said at least one acid is a mineral acid.

12. The method of claim 8 wherein the at least one acid includes a carboxylic acid selected from the group consisting of maleic, phthalic, oxalic, malonic, dichloroacetic and lactic acid and glycine.

13. The method of claim 8 wherein said reagent further comprises a chain-terminating antioxidant.

14. The method of claim 8 wherein said reagent further comprises an anti-microbial preservative.

15. The method of claim 4 wherein said mineral acid is hydrochloric acid.

16. The method of claim 11 wherein said mineral acid is hydrochloric acid.

* * * * *